(12) United States Patent
Pflaum

(10) Patent No.: US 6,324,254 B1
(45) Date of Patent: Nov. 27, 2001

(54) METHOD AND X-RAY DEVICE FOR PICKING UP X-RAY IMAGES OF A SUBSTANTIALLY RHYTHMICALLY MOVING VESSEL OR ORGAN

(75) Inventor: Michael Pflaum, Adelsdorf (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/431,215

(22) Filed: Nov. 1, 1999

(30) Foreign Application Priority Data

Nov. 23, 1998 (DE) .................................. 19853964

(51) Int. Cl.[7] .................................................. A61B 6/03
(52) U.S. Cl. .................................................. 378/95; 378/8
(58) Field of Search .................................. 378/4, 8, 98.8, 378/95

(56) References Cited

U.S. PATENT DOCUMENTS 5,228,070 * 7/1993 Mattson ................................ 378/95
5,832,051   11/1998 Lutz ....................................... 378/8
6,031,374 *  2/2000 Epstein et al. ....................... 324/306

FOREIGN PATENT DOCUMENTS

0026494 * 4/1981 (EP) ......................................... 378/8

* cited by examiner

Primary Examiner—Drew Dunn
(74) Attorney, Agent, or Firm—Schiff Hardin & Waite

(57) ABSTRACT

In a method and X-ray device for the pickup of X-ray images in an examination of a vessel or organ that moves substantially rhythmically, particularly for the determination of deposits in a vessel, such as a coronary vessel, the X-ray pickup system of an X-ray device is slowly moved along a circular orbit at an angular velocity of less than 6° per second, during which a number of digital X-ray images are picked up, with the image pickup being triggered by the vessel motion or organ motion acquired during the system movement or by an organ motion that causes the vessel motion, and a 3D image is reconstructed on the basis of the individual images, after the image pickup has ensued.

20 Claims, 1 Drawing Sheet

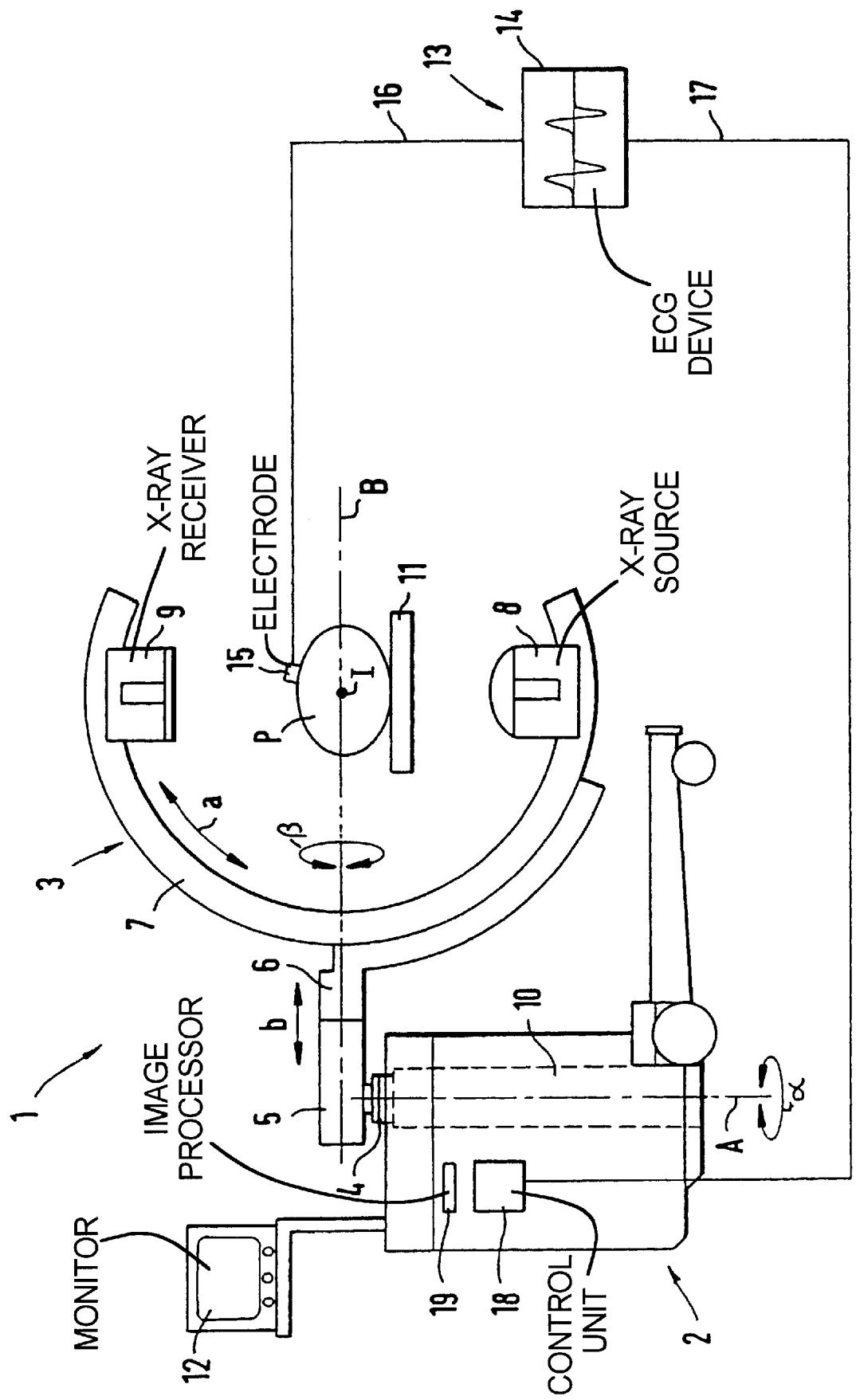

METHOD AND X-RAY DEVICE FOR PICKING UP X-RAY IMAGES OF A SUBSTANTIALLY RHYTHMICALLY MOVING VESSEL OR ORGAN

BACKGROUND OF THE INVENTION

1. Field of the Invention

The present invention directed to a method and x-ray device for the pick-up of X-ray images of a vessel or organ that move substantially rhythmically, particularly for determining deposits in a vessel, particularly in a coronary vessel.

2. Description of the Prior Art

Usually an invasive method is used for the examination of vessels or organs. For example, for displaying coronary chalk, or stenoses that are generated by coronary chalk, a contrast medium is injected into the coronary arteries in an angiographic examination, and at the same time, this body section is examined by means of X-radiation, and X-ray images are picked-up with a high image frequency (typically 30 images per second). The contrast medium bolus can be held in the vessels for approximately 4 through 5 seconds; therefore, such a high image frequency is used in order to obtain a sufficient number of images. Although this method is very sensitive and specific, a disadvantage is the invasiveness, the injection of a contrast medium. This method is not appropriate for a fast and simple routine examination (screening), of the type suitable, for example, for an annual check-up of a person who may be at risk of developing coronary blockage.

Further, the utilization of a computed tomography system is known for obtaining a display of the coronary chalk, however, a computed tomography system is a highly complex and expensive device, which is usually not present in, or is very difficult to integrate with examinations that ensue there within a cardiologic department of a hospital or similar facility. For example, German OS 196 22 075 discloses the utilization of a computed tomography system for the radiological examination of different heart phases.

SUMMARY OF THE INVENTION

An object of the present invention is to provide a method that enables a simple examination of a vessel or an organ.

This object is achieved in accordance with the invention in a method and X-ray device wherein a number of digital X-ray images are picked-up during a slow motion of an X-ray pick-up system of an X-ray device, this slow motion ensuing along an orbit with an angular velocity smaller than 6° per second, and wherein the image pick-up is triggered by the vessel motion or organ motion or by an organ motion causative for the vessel motion determined during the system motion, and wherein a 3D image is reconstructed based on the individual images subsequent to the image pick-up.

The method can be implemented by an X-ray device in the form of a rotation angiography device with an angiographic C-arm at which the X-ray pick-up system is arranged, which is usually present in cardiologic departments, and allows a simple examination. In contrast to the known operating method of a rotation angiography device in the context of the invasive examination described above, wherein the X-ray system optimally fast (with an angular velocity >45° per second) rotates around an angle of approximately 200°, the inventive X-ray pick-up system rotates as slow as possible so that a long time is available for the image pick-up, which is not problematic since the examination given the inventive method is not dependent on the time within which a contrast medium can be held in the vessel. In order to assure that the picked-up single images are each picked-up at a moment in which the rhythmically moving vessel or organ is in the same position as in the previous image, the vessel motion or organ motion is identified or monitored, and this organ motion is utilized for triggering the image pick-up. The heartbeat frequency, for example, can be acquired for the triggering, since the heart, which pumps the blood through the surrounding vessels, causes the rhythmic vessel motion. After the image pick-up, a three-dimensional image is inventively reconstructed in which plaque deposits which may be present in the vessel can be recognized. Therefore, the inventive method advantageously uses the X-ray system and X-ray pick-up system that are known and utilized in the cardiology in order to be able to examine and show rhythmically moving vessels or organs with a non-invasive examination.

The movements of the X-ray image pickup system can advantageously ensue with an angular velocity <2° per second, particularly with 0.50 per second, and the speed of movement of the X-ray image pickup system can be selected dependent on the frequency of movement of the acquired vessel motions and organ motions, i.e. the angular velocity with which the image pick-up system moves can definitely be selected all the higher, the higher the heart frequency is. The speed of movement should be selected such that at least 300 images, particularly at least 400 images, are acquired during a motion cycle of the X-ray image pickup system in order to obtain a sufficient number of quasi "stroboscopic" still image presentations of the heart, which are produced due to the motion triggering, for the 3D reconstruction. Inventively, the X-ray image pickup system itself can rotate around an angle of at least 150°, particularly of at least 200°.

The inventive X-ray device for the pick-up of X-ray images in a vessel examination or organ examination of a substantially rhythmically moving vessel or organ, particularly for the determination of deposits in a vessel, particularly in a coronary vessel, includes an X-ray image pickup system, which has an X-ray source and an X-ray receiver for the pick-up of digital 2D projection images from different projection angles of a subject to be examined and which, for this purpose, can be moved along a circular orbit with an angular velocity of less than 6° per second, an image processor for the reconstruction of a 3D image based on the 2D projection images, a control unit that controls the image pick-up mode, and a motion detection system for acquiring a vessel motion or organ motion or an organ motion that causes a vessel motion, which generates an output of motion-dependent signals. The motion detection system has a communication connection with the control unit, which also controls the movement of the X-ray image pickup system, and supply motion-dependent trigger signals thereto. The image pick-up mode is controllable dependent on the trigger signals. According to the invention, motion detection system can be an ECG device, with the heartbeat frequency being acquired for the generation of the trigger signals. The heart motion is relevant in examining the coronary arteries since it is this organ motion that causes the coronary vessel motion. Moreover, it is also possible to examine the heart or the heart muscle itself and the ventricles or the ventricle function; in this case, the heartbeat frequency also is acquired. To the extent that soft tissue resolution is sufficient in the reconstruction image generation, non-invasive examinations of the heart itself also can be undertaken with the inventive method and with the inventive device.

The invention is also directed to utilization of an X-ray device of the described type for the non-invasive examination of moving vessels that are close to the heart, particularly the coronary vessels, as well as the heart and the heart chambers themselves.

DESCRIPTION OF THE DRAWINGS

The single FIGURE is a schematic block diagram of an X-ray device constructed in accordance with the principles of the present invention and operating in accordance with the inventive method.

DESCRIPTION OF THE PREFERRED EMBODIMENTS

The single figure shows an inventive X-ray device 1 in the form of a rotation angiography device 2 with a C-arm system 3. A holder 5 is arranged at a column 4 that can be rotated around a longitudinal axis A (double arrow α). A support 6 is arranged at the holder 5 for supporting a C-arm 7 that exhibits an isocenter 1. The C-arm 7 has an X-ray image pickup system formed by an X-ray source 8 and an X-ray receiver 9 that are respectively mounted at the opposite ends of the C-arm 7. The X-ray receiver 9 can be an image amplifier camera system or can also be a solid-state detector, for example. The X-ray source 8 and the X-ray receiver 9 are arranged relative to one another such that a central beam of an X-ray bundle that emanates from the X-ray source 8 is incident approximately centrally on the X-ray receiver 9. The C-arm 7, in a known way, is motor-adjustable in the direction of the double arrow 'a' along its circumference in a way that is not shown in greater detail, and is mounted at the support 6. The support 6, in turn, can be rotated (in a way also known) around a common axis B of the holder 5 and the support 6 (double arrow β, angulation) and, in the direction of the axis B, is displaceably mounted at the holder 6. The C-arm 7 is vertically adjustable by a lifting unit 10 that engages the column 4.

The X-ray device 1 is provided for the generation of 3D images of a body area of a patient P lying on a patient support 11 (only schematically shown in the figure). The 3D images are reconstructed from 2D projections of the body area from different projection angles, which are acquired with the X-ray source 8 and the X-ray receiver 9 and can be displayed by a monitor 12. The C-arm 7 and therewith the X-ray image pickup system, along the double arrow "a" around an angular range of approximately 200°, and is motor-adjusted around the body area of the patient P to be examined for the pick-up of the 2D projection images from different projection angles, the images from the projection images being picked up during the adjusting movement. The adjusting movement ensues very slowly, with an angular velocity of less than 6° per second for example, preferably 0.5° per second. The projection images are picked up during this considerably long moving time, which amounts to 400 seconds total given an adjustment of 200°.

Since rhythmically moving vessels and organs, such as the coronary vessels for example, which move due to the rhythmically pumped blood, are to be examined with the inventive device, it is necessary to obtain projection images that respectively show the vessel in the same position, for the exact 3D reconstruction. For this purpose, a motion detection system 13 are provided by means of which the vessel motion or the motion of an organ, which causes the motion of the vessel to be examined, can be acquired. An ECG (electrocardiogram) device 14 is utilized in the shown example, which ECG has one or more body electrodes 15, which are externally secured in the area of the heart at the patient P and which supply motion-dependent signals via a corresponding signal line 16 (as shown in the figure). Based on the thus detected motion, trigger signals are generated by the ECG device 14, these trigger signals being sent to a control unit 18 via a further data line 17 (schematically shown in the figure). In the exemplary embodiment, this control unit 18 controls the movement of the C-arm 7 and controls the image pick-up mode. The image pick-up is then undertaken dependent on the supplied trigger signals, i.e. it is assured that the image is always picked up at the same moment in the vessel motion phase. For example, the individual peaks or the zero-axis crossings of the exemplarily shown heart rhythm curve can serve as trigger signal. If it is assumed, as described above, that the X-ray image pickup system has a moving time of 400 seconds, about 400 2D projection images are obtained given an average heartbeat frequency of 60 beats per minute, but the number certainly can be somewhat higher or lower dependent on the heartbeat frequency of the patient. In any case, a sufficient number of images is obtained in order to create a good 3D reconstruction display with small contrast differences and sufficient resolution. Thus, the coronary vessels, which move very fast, can be anatomically correctly reconstructed within a 3D display. An image processor 19 is provided for the reconstruction; the image signals obtained by the X-ray receiver 9 forwarded to the image processor 19, which, after completion of the image pick-up procedure, processes these signals to form a 3D image that is then displayed at the monitor 12.

Further, the control unit 18 controls the speed of movement of the X-ray image pickup system dependent on the heartbeat frequency (the acquired organ motion) so that it is assured that the minimum number of 2D projection images required will always be obtained by adaptation of the speed. For example, if the heartbeat frequency is high, the angular velocity can be increased, and vice versa.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for picking up X-ray images of a substantially rhythmically moving vessel or organ, comprising the steps of:

slowly rotating an X-ray image pick-up system, having an X-ray source and an X-ray receiver, around a subject in a circular path at an angular velocity of less than 6° per second and obtaining a plurality of digital X-ray images of said subject during said slow rotation, said subject containing a vessel or an organ exhibiting substantially rhythmic movement;

triggering pick up of the respective images in said plurality of digital X-ray images dependent on said substantially rhythmic movement; and reconstructing a three-dimensional image from said plurality of digital X-ray images after completing said slow rotation.

2. A method as claimed in claim 1 comprising conducting said slow rotation at an angular velocity of less than 2° per second.

3. A method as claimed in claim 1 comprising conducting said slow rotation at an angular velocity of less than 0.5° per second.

4. A method as claimed in claim 1 comprising controlling said slow rotation of said X-ray image pick-up system dependent on a frequency of said substantially rhythmic movement of said vessel or organ.

5. A method as claimed in claim 4 comprising selecting said angular velocity so that said plurality of digital X-ray images comprises at least 300 digital X-ray images.

6. A method as claimed in claim 4 comprising selecting said angular velocity so that said plurality of digital X-ray images comprises at least 400 digital X-ray images.

7. A method as claimed in claim 1 comprising rotating said X-ray image pick-up system through an angle of at least 150°.

8. A method as claimed in claim 1 comprising rotating said X-ray image pick-up system through an angle of at least 200°.

9. A method as claimed in claim 1 comprising monitoring a heartbeat frequency of a heart in said subject and using said heartbeat frequency as said substantially rhythmic movement for triggering pick-up of the respective images in said plurality of digital X-ray images.

10. A method as claimed in claim 1 comprising mounting said X-ray source and said X-ray receiver on a C-arm and rotating said C-arm around a rotational axis to produce said slow rotation of said X-ray image pick-up system.

11. An X-ray device for picking up X-ray images of a vessel or organ exhibiting substantially rhythmic movement, comprising:

an X-ray image pick-up system having an X-ray source and an X-ray receiver for obtaining a plurality of two-dimensional projection images from different projection angles of a subject, said subject containing a vessel or an organ exhibiting substantially rhythmic movement;

means for rotating said X-ray image pick-up system around said subject at an angular velocity of less than 6° per second, said X-ray receiver obtaining said plurality of two-dimensional projection images during said rotation;

an image processor, supplied with said plurality of two-dimensional images, for reconstructing a three-dimensional image of said vessel or organ from said plurality of two-dimensional images;

a monitor for identifying said substantially rhythmic motion associated with said vessel or organ and generating a motion-dependent signal corresponding to said motion; and a control unit, supplied with said motion-dependent signal, for generating trigger signals to said X-ray image pick-up system to trigger pick up of said plurality of two-dimensional projection images at a same time in each motion phase of said vessel or organ.

12. An X-ray device as claimed in claim 11 wherein said means for rotating said X-ray image pick-up system rotates said image pick-up system rotates said X-ray image pick-up system at an angular velocity of less than 2° per second.

13. An X-ray device as claimed in claim 11 wherein said means for rotating said X-ray image pick-up system rotates said image pick-up system rotates said X-ray image pick-up system at an angular velocity of less than 0.5° per second.

14. An X-ray device as claimed in claim 11 wherein said control unit also controls the angular velocity of the rotation of said X-ray image pick-up system and adjusts said angular velocity dependent on a frequency of said substantially rhythmic movement of said vessel or organ identified from said motion-dependent signal.

15. An X-ray device as claimed in claim 11 wherein said means for rotating rotates said image pick-up system at an angular velocity so that said plurality of two-dimensional projection images comprises at 300 two-dimensional projection images.

16. An X-ray device as claimed in claim 11 wherein said means for rotating rotates said image pick-up system at an angular velocity so that said plurality of two-dimensional projection images comprises at 400 two-dimensional projection images.

17. An X-ray device as claimed in claim 11 wherein said X-ray image pick-up system is rotatable through an angle around said subject of at least one 150°.

18. An X-ray device as claimed in claim 11 wherein said X-ray image pick-up system is rotatable through an angle around said subject of at least one 200°.

19. An X-ray device as claimed in claim 11 wherein said monitor comprises an ECG device and wherein said motion-dependent signal comprises a signal identifying heartbeat frequency.

20. An X-ray device as claimed in claim 11 wherein said X-ray image pick-up system comprises a rotation angiography device with said X-ray source and said X-ray receiver mounted at opposite ends of a C-arm.

\* \* \* \* \*